(12) United States Patent
Ritchie et al.

(10) Patent No.: US 10,194,655 B2
(45) Date of Patent: Feb. 5, 2019

(54) AORTIC CANNULA FOR EX VIVO ORGAN CARE SYSTEM

(71) Applicant: TransMedics, Inc., Andover, MA (US)

(72) Inventors: Greg Ritchie, Rowley, MA (US); Vincent Lambert, II, Salisbury, MA (US); Richard Bringham, North Andover, MA (US); John Sullivan, Groton, MA (US); Waleed H. Hassanein, North Andover, MA (US)

(73) Assignee: TRANSMEDICS, INC., Andover, MA (US)

( * ) Notice: Subject to any disclaimer, the term of this patent is extended or adjusted under 35 U.S.C. 154(b) by 155 days.

(21) Appl. No.: 15/258,194

(22) Filed: Sep. 7, 2016

(65) Prior Publication Data

US 2017/0064943 A1    Mar. 9, 2017

Related U.S. Application Data

(60) Provisional application No. 62/215,825, filed on Sep. 9, 2015.

(51) Int. Cl.
*A01N 1/02* (2006.01)
(52) U.S. Cl.
CPC ................... *A01N 1/0247* (2013.01)
(58) Field of Classification Search
CPC .. A61N 1/0236; A61N 1/0242; A61N 1/0247; A61M 1/00; A61M 2210/125; A61M 2210/127; A61F 2/24
USPC ....................................................... 604/6.16
See application file for complete search history.

(56) References Cited

U.S. PATENT DOCUMENTS

| 3,253,595 | A | 5/1966 | Keller, Jr. et al. |
| 3,388,803 | A | 6/1968 | Scott |
| 3,406,531 | A | 10/1968 | Koski et al. |
| 3,468,136 | A | 9/1969 | Koski et al. |
| 3,537,956 | A | 11/1970 | Falcone |
| 3,545,221 | A | 12/1970 | Koski et al. |
| 3,545,605 | A | 12/1970 | Robins |
| 3,587,567 | A | 6/1971 | Schiff |
| 3,607,646 | A | 9/1971 | de Roissart |
| 3,632,473 | A | 1/1972 | Belzer et al. |
| 3,639,084 | A | 2/1972 | Goldhaber |
| 3,654,085 | A | 4/1972 | Fritz et al. |

(Continued)

FOREIGN PATENT DOCUMENTS

| CA | 2881613 | 11/2007 |
| CN | 1232723 A | 10/1999 |

(Continued)

OTHER PUBLICATIONS

"2002 Design & Engineering Awards, Portable Organ Preservation System", Science (2002) (1 page).

(Continued)

*Primary Examiner* — Philip R Wiest
(74) *Attorney, Agent, or Firm* — Wilmer Cutler Pickering Hale and Dorr LLP

(57) ABSTRACT

The invention provides, in various embodiments, devices and methods relating to ex-vivo organ care. In certain embodiments, the invention relates to aortic cannulas for use in perfusion systems to return perfusate to the heart or delivering perfusate from the heart while the organ is sustained ex vivo at physiologic or near-physiologic conditions.

22 Claims, 12 Drawing Sheets

(56) References Cited

U.S. PATENT DOCUMENTS

| | | |
|---|---|---|
| 3,660,241 A | 5/1972 | Michielsen |
| 3,738,914 A | 6/1973 | Thorne et al. |
| 3,772,153 A | 11/1973 | De Roissart |
| 3,777,507 A | 12/1973 | Burton et al. |
| 3,843,455 A | 10/1974 | Bier et al. |
| 3,851,646 A | 12/1974 | Sarns |
| 3,881,990 A | 5/1975 | Burton et al. |
| 3,995,444 A | 12/1976 | Clark et al. |
| 4,186,565 A | 2/1980 | Toledo-Pereyra |
| 4,231,354 A | 11/1980 | Kurtz et al. |
| 4,415,556 A | 11/1983 | Bretschneider |
| 4,598,697 A | 7/1986 | Numazawa et al. |
| 4,605,644 A | 8/1986 | Foker |
| 4,666,425 A | 5/1987 | Fleming |
| 4,719,201 A | 1/1988 | Foker |
| 4,723,939 A | 2/1988 | Anaise |
| 4,745,759 A | 5/1988 | Bauer et al. |
| 4,759,371 A | 7/1988 | Franetzki |
| 4,801,299 A | 1/1989 | Brendel et al. |
| 4,847,470 A | 7/1989 | Bakke |
| 4,920,044 A | 4/1990 | Bretan, Jr. |
| 5,051,352 A | 9/1991 | Martindale et al. |
| 5,066,578 A | 11/1991 | Wikman-Coffelt |
| 5,141,847 A | 8/1992 | Sugimachi et al. |
| 5,145,771 A | 9/1992 | Lemasters et al. |
| 5,157,930 A | 10/1992 | McGhee et al. |
| 5,200,398 A | 4/1993 | Strasberg et al. |
| 5,217,860 A | 6/1993 | Fahy et al. |
| 5,285,657 A | 2/1994 | Bacchi et al. |
| 5,306,711 A | 4/1994 | Andrews |
| 5,326,706 A | 7/1994 | Yland et al. |
| 5,338,662 A | 8/1994 | Sadri |
| 5,356,593 A | 10/1994 | Heiberger et al. |
| 5,356,771 A | 10/1994 | O'Dell |
| 5,358,931 A | 10/1994 | Rubinsky et al. |
| 5,362,622 A | 11/1994 | O'Dell et al. |
| 5,370,989 A | 12/1994 | Stern et al. |
| 5,381,510 A | 1/1995 | Ford et al. |
| 5,385,821 A | 1/1995 | O'Dell et al. |
| 5,395,314 A | 3/1995 | Klatz et al. |
| 5,405,742 A | 4/1995 | Taylor |
| 5,407,669 A | 4/1995 | Lindstrom et al. |
| 5,407,793 A | 4/1995 | Del Nido et al. |
| 5,472,876 A | 12/1995 | Fahy |
| 5,473,791 A | 12/1995 | Holcomb et al. |
| 5,494,822 A | 2/1996 | Sadri |
| 5,498,427 A | 3/1996 | Menasche |
| 5,505,709 A | 4/1996 | Funderburk et al. |
| 5,514,536 A | 5/1996 | Taylor |
| 5,552,267 A | 9/1996 | Stern et al. |
| 5,554,123 A | 9/1996 | Herskowitz |
| 5,554,497 A | 9/1996 | Raymond |
| 5,571,801 A | 11/1996 | Segall et al. |
| 5,584,804 A | 12/1996 | Klatz et al. |
| 5,586,438 A | 12/1996 | Fahy |
| 5,588,816 A | 12/1996 | Abbott et al. |
| 5,599,173 A | 2/1997 | Chen et al. |
| 5,599,659 A | 2/1997 | Brasile et al. |
| 5,613,944 A | 3/1997 | Segall et al. |
| 5,643,712 A | 7/1997 | Brasile |
| 5,654,266 A | 8/1997 | Chen et al. |
| 5,656,420 A | 8/1997 | Chien |
| 5,679,565 A | 10/1997 | Mullen et al. |
| 5,693,462 A | 12/1997 | Raymond |
| 5,698,536 A | 12/1997 | Segall et al. |
| 5,699,793 A | 12/1997 | Brasile |
| 5,702,881 A | 12/1997 | Brasile et al. |
| 5,716,378 A | 2/1998 | Minten |
| 5,723,281 A | 3/1998 | Segall et al. |
| 5,733,894 A | 3/1998 | Segall et al. |
| 5,747,071 A | 5/1998 | Segall et al. |
| 5,752,929 A | 5/1998 | Klatz et al. |
| 5,770,149 A | 6/1998 | Raible |
| 5,776,063 A | 7/1998 | Dittrich et al. |
| 5,786,136 A | 7/1998 | Mayer |
| 5,787,544 A | 8/1998 | Meade |
| 5,807,737 A | 9/1998 | Schill et al. |
| 5,823,799 A | 10/1998 | Tor et al. |
| 5,843,024 A | 12/1998 | Brasile |
| 5,856,081 A | 1/1999 | Fahy |
| 5,882,328 A | 3/1999 | Levy et al. |
| 5,965,433 A | 10/1999 | Gardetto et al. |
| 5,998,240 A | 12/1999 | Hamilton et al. |
| 6,024,698 A | 2/2000 | Brasile |
| 6,034,109 A | 3/2000 | Ramasamy et al. |
| 6,042,550 A | 3/2000 | Haryadi et al. |
| 6,046,046 A | 4/2000 | Hassanein |
| 6,050,987 A | 4/2000 | Rosenbaum |
| 6,100,082 A | 8/2000 | Hassanein |
| 6,110,139 A | 8/2000 | Loubser |
| 6,110,504 A | 8/2000 | Segall et al. |
| 6,144,444 A | 11/2000 | Haworth et al. |
| 6,168,877 B1 | 1/2001 | Pedicini et al. |
| 6,365,338 B1 | 4/2002 | Bull et al. |
| 6,375,611 B1 | 4/2002 | Voss et al. |
| 6,375,613 B1 | 4/2002 | Brasile |
| 6,389,308 B1 | 5/2002 | Shusterman |
| 6,402,461 B1 | 6/2002 | Tebby |
| 6,475,716 B1 | 11/2002 | Seki |
| 6,490,880 B1 | 12/2002 | Walsh |
| 6,492,103 B1 | 12/2002 | Taylor |
| 6,492,745 B1 | 12/2002 | Colley, III et al. |
| 6,524,785 B1 | 2/2003 | Cozzone et al. |
| 6,569,615 B1 | 5/2003 | Thatte et al. |
| 6,582,953 B2 | 6/2003 | Brasile |
| 6,600,941 B1 | 7/2003 | Khuri |
| 6,609,987 B1 | 8/2003 | Beardmore |
| 6,631,830 B2 | 10/2003 | Ma et al. |
| 6,642,045 B1 | 11/2003 | Brasile |
| 6,673,594 B1 | 1/2004 | Owen et al. |
| 6,696,238 B2 | 2/2004 | Murphy et al. |
| 6,740,484 B1 | 5/2004 | Khirabadi et al. |
| 6,783,328 B2 | 8/2004 | Lucke et al. |
| 6,792,309 B1 | 9/2004 | Noren |
| 6,794,124 B2 | 9/2004 | Steen |
| 6,811,965 B2 | 11/2004 | Vodovotz et al. |
| 6,878,339 B2 | 4/2005 | Akiyama et al. |
| 6,925,324 B2 | 8/2005 | Shusterman |
| 6,953,655 B2 | 10/2005 | Hassanein et al. |
| 6,974,436 B1 | 12/2005 | Aboul-Hosn et al. |
| 7,001,354 B2 | 2/2006 | Suzuki et al. |
| 7,008,380 B1 | 3/2006 | Rees et al. |
| 7,238,165 B2 | 7/2007 | Vincent et al. |
| 7,316,666 B1 | 1/2008 | Entenman et al. |
| 7,452,711 B2 | 11/2008 | Daykin |
| 7,572,622 B2 | 8/2009 | Hassanein et al. |
| 7,651,835 B2 | 1/2010 | Hassanein et al. |
| 8,304,181 B2 | 11/2012 | Hassanein et al. |
| 8,409,846 B2 | 4/2013 | Hassanein et al. |
| 8,420,380 B2 | 4/2013 | Fishman et al. |
| 8,465,970 B2 | 6/2013 | Hassanein et al. |
| 8,535,934 B2 | 9/2013 | Hassanein et al. |
| 8,585,380 B2 | 11/2013 | Hassanein et al. |
| 8,822,203 B2 | 9/2014 | Hassanein et al. |
| 9,215,867 B2 | 12/2015 | Hassanein et al. |
| 9,457,179 B2 | 10/2016 | Hassanein et al. |
| 9,462,802 B2 | 10/2016 | Fishman et al. |
| 2001/0003652 A1 | 6/2001 | Freeman |
| 2001/0025191 A1 | 9/2001 | Montgomery |
| 2002/0012988 A1 | 1/2002 | Brasile |
| 2002/0102720 A1 | 8/2002 | Steen |
| 2002/0132220 A1 | 9/2002 | Berens et al. |
| 2002/0151950 A1 | 10/2002 | Okuzumi |
| 2002/0164795 A1 | 11/2002 | Gen |
| 2002/0177117 A1 | 11/2002 | Wolf |
| 2002/0187132 A1 | 12/2002 | Mcgregor et al. |
| 2003/0040665 A1 | 2/2003 | Khuri et al. |
| 2003/0050689 A1 | 3/2003 | Matson |
| 2003/0053998 A1 | 3/2003 | Daemen et al. |
| 2003/0073227 A1 | 4/2003 | Hull et al. |
| 2003/0074760 A1 | 4/2003 | Keller |
| 2003/0086830 A1 | 5/2003 | Haywood et al. |
| 2003/0111604 A1 | 6/2003 | Quek |
| 2003/0135152 A1 | 7/2003 | Kollar et al. |

(56) References Cited

U.S. PATENT DOCUMENTS

| | | |
|---|---|---|
| 2003/0147466 A1 | 8/2003 | Liang |
| 2004/0015042 A1 | 1/2004 | Vincent et al. |
| 2004/0017658 A1 | 1/2004 | Lo et al. |
| 2004/0018966 A1 | 1/2004 | Segall et al. |
| 2004/0029096 A1 | 2/2004 | Steen |
| 2004/0038192 A1 | 2/2004 | Brasile |
| 2004/0058432 A1 | 3/2004 | Owen et al. |
| 2004/0082057 A1 | 4/2004 | Alford et al. |
| 2004/0086578 A1 | 5/2004 | Segall et al. |
| 2004/0102415 A1 | 5/2004 | Thatte et al. |
| 2004/0102678 A1 | 5/2004 | Haindl |
| 2004/0106958 A1 | 6/2004 | Mathis et al. |
| 2004/0110800 A1 | 6/2004 | Bril et al. |
| 2004/0115689 A1 | 6/2004 | Augello et al. |
| 2004/0138542 A1 | 7/2004 | Khuri et al. |
| 2004/0168341 A1 | 9/2004 | Petersen et al. |
| 2004/0170950 A1 | 9/2004 | Prien |
| 2004/0171138 A1 | 9/2004 | Hassanein et al. |
| 2004/0193096 A1 | 9/2004 | Cooper |
| 2004/0202993 A1 | 10/2004 | Poo et al. |
| 2004/0221719 A1 | 11/2004 | Wright et al. |
| 2004/0224298 A1 | 11/2004 | Brassil et al. |
| 2004/0235142 A1 | 11/2004 | Schein et al. |
| 2004/0236170 A1 | 11/2004 | Kim |
| 2004/0248281 A1 | 12/2004 | Wright et al. |
| 2005/0010118 A1 | 1/2005 | Toyoda et al. |
| 2005/0019917 A1 | 1/2005 | Toledo-Pereyra et al. |
| 2005/0142532 A1 | 6/2005 | Poo et al. |
| 2005/0147958 A1 | 7/2005 | Hassanein et al. |
| 2005/0153271 A1 | 7/2005 | Wenrich |
| 2005/0170019 A1 | 8/2005 | Roth |
| 2005/0182349 A1 | 8/2005 | Linde et al. |
| 2005/0187469 A1 | 8/2005 | Phillips |
| 2005/0253390 A1* | 11/2005 | Blazek ............... A61M 39/1011 285/420 |
| 2006/0039870 A1 | 2/2006 | Turner |
| 2006/0074470 A1 | 4/2006 | Bartels et al. |
| 2006/0121438 A1 | 6/2006 | Toledo-Pereyra et al. |
| 2006/0124130 A1 | 6/2006 | Bonassa |
| 2006/0134073 A1 | 6/2006 | Naka et al. |
| 2006/0148062 A1 | 7/2006 | Hassanein et al. |
| 2006/0154357 A1 | 7/2006 | Hassanein et al. |
| 2006/0154359 A1 | 7/2006 | Hassanein et al. |
| 2006/0160204 A1 | 7/2006 | Hassanein et al. |
| 2006/0292544 A1 | 12/2006 | Hassanein et al. |
| 2007/0196461 A1 | 8/2007 | Weers |
| 2007/0275364 A1 | 11/2007 | Hassanein et al. |
| 2008/0017191 A1 | 1/2008 | Davies et al. |
| 2008/0017194 A1 | 1/2008 | Hassanein et al. |
| 2008/0234768 A1 | 9/2008 | Hassanein et al. |
| 2008/0286746 A1 | 11/2008 | Poo et al. |
| 2009/0142830 A1 | 6/2009 | Yamashiro et al. |
| 2009/0143417 A1 | 6/2009 | Smith et al. |
| 2009/0197240 A1 | 8/2009 | Fishman et al. |
| 2009/0197241 A1 | 8/2009 | Fishman et al. |
| 2009/0197292 A1 | 8/2009 | Fishman et al. |
| 2009/0197324 A1 | 8/2009 | Fishman et al. |
| 2009/0197325 A1 | 8/2009 | Fishman et al. |
| 2009/0215022 A1 | 8/2009 | Page et al. |
| 2009/0312724 A1 | 12/2009 | Pipkin et al. |
| 2010/0056966 A1 | 3/2010 | Toth |
| 2010/0092939 A1 | 4/2010 | Belous et al. |
| 2011/0076666 A1 | 3/2011 | Brassil |
| 2011/0136096 A1 | 6/2011 | Hassanein et al. |
| 2011/0190572 A1 | 8/2011 | Brophy et al. |
| 2011/0212431 A1 | 9/2011 | Bunegin et al. |
| 2012/0277681 A1* | 11/2012 | Kravitz ............... A61B 17/122 604/175 |
| 2013/0011823 A1* | 1/2013 | Hassanein ............ A01N 1/0226 435/1.2 |
| 2013/0078710 A1 | 3/2013 | Hassanein et al. |
| 2013/0157248 A1 | 6/2013 | Fishman et al. |
| 2013/0295552 A1 | 11/2013 | Hassanein et al. |
| 2014/0017658 A1 | 1/2014 | Steinman et al. |
| 2014/0017660 A1 | 1/2014 | Steinman et al. |
| 2014/0135738 A1 | 5/2014 | Panian |
| 2015/0079580 A1 | 3/2015 | Hassanein et al. |
| 2015/0230453 A1 | 8/2015 | Fontes et al. |

FOREIGN PATENT DOCUMENTS

| | | |
|---|---|---|
| CN | 1269471 A | 10/2000 |
| DE | 4201259 A1 | 7/1993 |
| DE | 10121159 A1 | 11/2002 |
| EP | 0347923 | 12/1989 |
| EP | 0376763 | 7/1990 |
| EP | 1942726 A2 | 7/2008 |
| JP | H02-282301 A | 11/1990 |
| JP | 02-306901 A | 12/1990 |
| JP | H03-74302 A | 3/1991 |
| JP | 04-099701 A | 3/1992 |
| JP | H04-128201 A | 4/1992 |
| JP | 06-056601 | 3/1994 |
| JP | 06-305901 | 11/1994 |
| JP | 08-511012 | 11/1996 |
| JP | 2001061956 A | 3/2001 |
| JP | 2001516768 A | 10/2001 |
| JP | 2003-315220 A | 11/2003 |
| JP | 2004513889 A | 5/2004 |
| JP | 2004525290 A | 8/2004 |
| JP | 2004529938 A | 9/2004 |
| JP | 2008-515914 A | 5/2008 |
| JP | 2009-521931 A | 6/2009 |
| JP | 2011-511000 A | 4/2011 |
| JP | 2016-053030 | 4/2016 |
| JP | 6144238 B2 | 6/2017 |
| WO | WO-8805261 A1 | 7/1988 |
| WO | WO95/02326 | 1/1995 |
| WO | WO-9531897 A1 | 11/1995 |
| WO | WO-9618293 A1 | 6/1996 |
| WO | WO-9629865 A1 | 10/1996 |
| WO | WO-9746091 A1 | 12/1997 |
| WO | WO-9915011 A1 | 4/1999 |
| WO | WO-0022927 A1 | 4/2000 |
| WO | WO-0060936 A1 | 10/2000 |
| WO | WO-0226034 A2 | 4/2002 |
| WO | WO-02/35929 A1 | 5/2002 |
| WO | WO-02089571 A1 | 11/2002 |
| WO | WO-2004026031 A2 | 4/2004 |
| WO | WO-2006042138 A2 | 4/2006 |
| WO | WO-2006076590 A2 | 7/2006 |
| WO | WO-2006124820 A2 | 11/2006 |
| WO | WO-2007079185 A2 | 7/2007 |
| WO | WO-2007124044 A2 | 11/2007 |
| WO | WO-2008106724 A1 | 9/2008 |
| WO | WO-2009/099939 A2 | 8/2009 |
| WO | WO-2011072012 A2 | 6/2011 |
| WO | WO-2013068752 A2 | 5/2013 |
| WO | WO-2014059316 A1 | 4/2014 |
| WO | WO-2015154170 A1 | 10/2015 |

OTHER PUBLICATIONS

"Celsior™ Cold Storage Solution", Sangstat Medical Corporation (internet reference) (1999) (5 pages).
"History of Transplantation and Organ Preservation," Barr Laboratories, Inc. (2004), 4 pages.
"Human heart beats on its own outside body", USA Today (2001) (1 page).
"Human Heart Kept Alive Outside Body for First Time in Study of Portable Organ Preservation System™ at University of Pittsburgh Medical Center", UPMC, McGowan Institute for Regenerative Medicine (2001) (2 pages).
"Machine Keeps Human Kidney Alive for 24-Hours", American Academy of Anti-Aging Medicine, www.worldhealth.net, Aug. 25, 2001, Accessed Jul. 5, 2006, 1 page.
"Machine may be organ transplant breakthrough", USA Today (Aug. 2001), 1 page.
"New discovery in organ transplantation", MSNBC (2001), 1 page.
"The Nation: Warm-Storage Device May Aid Organ Transplants", Dow Jones Publications Library (2001), 1 page.

(56) References Cited

OTHER PUBLICATIONS

"ViaSpan (Belzer UW) Cold Storage Solution", Barr Laboratories, Inc. (2002), 2 pages.
"Warm storage for donor organs", University of Chicago Magazine (2001) (1 page).
Ahmad, N. et al., "A pathophysiologic study of the kidney tubule to optimize organ preservation solutions", Kidney International 66(1):77-90 (2004), 14 pages.
Aitchison, J.D. et al., "Nitric Oxide During Perfusion Improves Posttransplantation Function of Non-Heart-Beating Donor Lungs", Transplantation, 75(12):1960-1964, Jun. 27, 2003, 5 pages.
Ananthaswamy, A., "Machine keeps organs alive for longer", NewScientist.com, Aug. 16, 2001 (1 page).
Aoki, M. et al., "Anti-CD18 Attenuates Deleterious Effects of Cardiopulmonary Bypass and Hypothermic Circulatory Arrest in Piglets", J. Card. Surg. 10(Suppl):407-17 (1995) (11 pages).
Bando, K. et al., "Oxygenated perfluorocarbon, recombinant human superoxide dismutase, and catalase ameliorate free radical induced myocardial injury during heart preservation and transplantation", J. Thorac Cardiovasc Surg. 96:930-8 (Dec. 1988), 9 pages.
Barinov, E.F., "Hormonal-metabolic disturbances during biological preservation of the heart", Fiziologicheskii Zhurnal (Kiev), 29(3):293-299 (1983) (8 pages)—Russian Language with English Abstract.
Belzer, F.O., "Formula for Belzer MPS Solution", University of Wisconsin-Madison Organ Preservation (internet reference) (2003) (2 pages).
Benichou, J. et al., "Canine and Human Liver Preservation for 6 to 18 HR by Cold Infusion", Transplantation, 24(6):407-411 (Dec. 1977) (5 pages).
Birkett, D. et al., "The Fatty Acid Content and Drug Binding Characteristics of Commercial Albumin Preparations", Clinica Chimica Acta 85:253-258 (1978), 6 pages.
Blanchard, J.M. et al., "Techniques for Perfusion and Storage of Heterotopic Heart Transplants in Mice", Microsurgery, 6:169-174 (1985), 6 pages.
Boggi, U. et al., "Pancreas Preservation with University of Wisconsin and Celsior Solutions", Transplantation Proceedings 36(3):563-565 (2004), 3 pages.
Boggi, U. et al., "Pancreas Preservation With University of Wisconsin and Celsior Solutions: A Single-Center, Prospective, Randomized Pilot Study", Transplantation, 77(8):1186-1190 (2004), 5 pages.
Boyle, E.M. Jr. et al., "Ischemia-Reperfusion Injury", Ann. Thorac. Surg. 64:S24-S30 (1997), 7 pages.
Brandes, H. et al. "Influence of High Molecular Dextrans on Lung Function in an ex Vivo Porcine Lung Model," Journal of Surgical Research, 101(2):225-231 (2001), published online Oct. 29, 2001 (7 pages).
Brasile, L. et al., "Organ Preservation Without Extreme Hypothermia Using an Oxygent™ Supplemented Perfusate", Art. Cells, Blood Subs., and Immob. Biotech., 22(4):1463-68 (1994), 6 pages.
Burt, J.M. et al, "Myocardial function after preservation for 24 hours", J. Thorac. Cardiovasc Surg., 92(2):238-46 (1986), 9 pages.
Calhoon, J.H. et al., "Twelve-Hour Canine Heart Preservation With a Simple, Portable Hypothermic Organ Perfusion Device", Ann. Thorac. Surg., 62:91-3 (1996), 3 pages.
Canelo R. et al., "Experience with Hystidine Tryptophan Ketoglutarate Versus University Wisconsin Preservation Solutions in Transplantation", Int. Surg. 88(3):145-151 (2003), 8 pages.
Carrier, B., "Chapter 4: Hypoxia and Oxygenation", Alaska Air Medical Escort Training Manual, Fourth Edition, pp. 71-82, 2006, 12 pages.
Chambers, D.J. et al., "Long-Term Preservation of the Heart: The Effect of Infusion Pressure During Continuous Hypothermic Cardioplegia", The Journal of Heart and Lung Transplantation, 11(4):665-75 (1992), 11 pages.
Chen, F. et al., "Development of New Organ Preservation Solutions in Kyoto University", Yonsei Medical Journal, 45(6):1107-14 (2004), 8 pages.

Chien, S. et al., "A simple technique for multiorgan preservation", The Journal of Thoracic and Cardiovascular Surgery, 95(1):55-61 (1988), 7 pages.
Chien, S. et al., "Canine Lung Transplantation After More than Twenty-four Hours of Normothermic Preservation", The Journal of Heart and Lung Transplantation, 16(3):340-51 (1997), 12 pages.
Chien, S. et al., "Functional Studies of the Heart During a 24-Hour Preservation Using a New Autoperfusion Preparation", The Journal of Heart and Lung Transplantation, 10(3):401-8 (1991), 8 pages.
Christophi, C. et al., "A Comparison of Standard and Rapid Infusion Methods of Liver Preservation During Multi-Organ Procurement", Aust. N.Z. J. Surg., 61(9):692-694 (1991), 3 pages.
Cimino, Adria, "Doctor develops device to preserve donated organs", Mass High Tech (Sep. 17, 2001), 2 pages.
CNN.com, "Heart kept beating outside body", Associated Press (2001), 2 pages.
Collins, B.H., "Organ Transplantation: What Is the State of the Art?", Annals of Surgery, 238(6 Suppl):S72-S89 (2003), 18 pages.
Cronin, D.C. et al., "Chapter 21: Liver Transplantation at the University of Chicago", Clinical Transplants 231-238 (1999), 9 pages.
Daemen, J.H.C. et al., "Short-term outcome of kidney transplants from non-heart-beating donors after preservation by machine perfusion", Transpl. Int. 9(Supp 1):S76-S80 (1996), 5 pages.
Definition of Examine, Merriam-Webster Dictionary on-line. www.merriam-webster.com/dictionary/examine, Printed Feb. 9, 2011, (1 page).
Demertzis, S. et al., "University of Wisconsin Versus St. Thomas' Hospital Solution for Human Donor Heart Preservation", Ann Thorac Surg 55:1131-7 (1993), 7 pages.
Den Butter, G. et al., "Comparison of solutions for preservation of the rabbit liver as tested by isolated perfusion", Transpl. Int. 8(6):466-471 (1995), 6 pages.
Denham, B.S. et al., "Twenty-Four Hour Canine Renal Preservation by Pulsatile Perfusion, Hypothermic Storage, and Combinations of the Two Methods", Transplantation Proceedings, 9(3):1553-1556 (1977), 4 pages.
Dobrian, A. et al., "In vitro formation of oxidatively-modified and reassembled human low-density lipoproteins: antioxidant effect of albumin", Biochimica et Biophysica Acta (BBA) 1169:12-24 (1993), 13 pages.
Drexler, H. et al., "Effect of L-arginine on coronary endothelial function in cardiac transplant recipients. Relation to vessel wall morphology," Circulation 89(4):1615-1623 (1994) (10 pages).
Egan, T. M. et al., "Ex Vivo Evaluation of Human Lungs for Transplant Suitability", Ann Thorac Surg, vol. 81, No. 4, pp. 1205-1213 (Apr. 2006) (9 pages).
Eiseman, B. et al., "A disposable liver perfusion chamber", Surgery 60(6):1183-1186 (Dec. 1966), 4 pages.
Engelman, R.M. et al., "Influence of Steroids on Complement and Cytokine Generation After Cardiopulmonary Bypass", Ann Thorac Surg 60(3):801-04 (1995) (4 pages).
Eurpean Search Report for European Patent Application No. 08795820.3 dated Apr. 17, 2014 (6 pages).
Eurpean Search Report for European Patent Application No. 09707471.0 dated May 27, 2014 (7 pages).
Eurpean Search Report issued in EP12770852.7, dated Sep. 23, 2014, 8 pages.
Fabregas, L., "UPMC tests machine to aid heart transplants", Pittsburgh Tribune-Review (Mar. 5, 2002), pages.
Faggian, G. et al., "Donor Organ Preservation in High-Risk Cardiac Transplantation", Transplantation Proceedings 36:617-619 (2004), 3 pages.
Featherstone, R.L. et al. "Comparison of Phosphodiesterase Inhibitors of Differing Isoenzyme Selectivity Added to St. Thomas' Hospital Cardioplegic Solution Used for Hypothermic Preservation of Rat Lungs", Am J Respir Crit Med, Mar. 2000, 162(3):850-856 (7 pages).
Fehrenberg, C. et al., "Protective Effects of B2 Preservation Solution in Comparison to a Standard Solution (Histidine-Tryptophan-Ketoglutarate/Bretschneider) in a Model of Isolated Autologous Hemoperfused Porcine Kidney", Nephron Physiol 96:52-58 (2004) (7 pages).

(56) References Cited

OTHER PUBLICATIONS

Ferrera, R. et al., "Comparison of Different Techniques of Hypothermic Pig Heart Preservation", Ann Thorac Surg 57(5):1233-1239 (1994), 7 pages.
File History for U.S. Appl. No. 60/616,835, filed Oct. 7, 2004.
File History for U.S. Appl. No. 60/694,971, filed Jun. 28, 2005.
File History for U.S. Appl. No. 60/725,168, filed Oct. 6, 2005 (699 pages).
Finn, A. et al., "Effects of Inhibition of Complement Activation Using Recombinant Soluble Complement Receptor 1 on Neutrophil CD11B/CD18 and L-Selectin Expression and Release of Interleukin-8 and Elastase in Simulated Cardiopulmonary Bypass", J Thorac Cardiovasc Surg 111(2):451-459 (1996), 9 pages.
Fourcade, C. et al., "Nouvelle Méthode De Conservation Du Rein Avec Une Solution De Collins", A New Method of Kidney Preservation with Collins' Solution, Biomed. 21(7):308-11 (1974), English Abstract, 5 pages.
Fraser, C.D. Jr. et al., "Evaluation of Current Organ Preservation Methods for Heart-Lung Transplantation", Transplantation Proceedings, 20(1 Suppl. 1):987-990 (1988), 4 pages.
Glucose, The Merck Index, 11th ed. Entry 4353 (pp. 699-700) (1989), 3 pages.
Grynberg, A. et al., "Fatty Acid Oxidation in the Heart", Journal of Cardiovascular Pharmacology, 28(Suppl. 1):S11-S17 (1996) (8 pages).
Guarrera, J.V. et al., "Pulsatile Machine Perfusion With Vasosol Solution Improves Early Graft Function After Cadaveric Renal Transplantation", Transplantation 77(8):1264-1268 (2004), 5 pages.
Gundry, S.R. et al., "Successful Transplantation of Hearts Harvested 30 Minutes After Death From Exsanguination", Ann Thorac Surg 53(5):772-775 (1992), 4 pages.
Habazettl, H. et al., "Improvement in Functional Recovery of the Isolated Guinea Pig Heart After Hyperkalemic Reperfusion With Adenosine", J Thorac Cardiovasc Surg 111(1):74-84 (1996) (11 pages).
Hachida, M. et al., Abstract "Efficacy of myocardial preservation using HTK solution in continuous 120 min cross-clamping method-a comparative study with GIK method", Nippon Kyobu Geka Gakkai Zasshi. 41(9):1495-1501 (1993), Retrieved on Jul. 2, 2006, 1 page.
Hardesty, R.L. et al., Original Communications, "Autoperfusion of the heart and lungs for preservation during distant procurement", J Thorac Cardiovasc Surg, 93(1):11-18 (1987) (8 pages).
Hartman, J.C., "The Role of Bradykinin and Nitric Oxide in the Cardioprotective Action of ACE Inhibitors", Ann Thorac Surg 60:789-792 (1995), 4 pages.
Hassanein, W.H. et al., "A Novel Approach for 12 Hour Donor Heart Preservation", Presented at the 70th Scientific Sessions of The American Heart Association, Abstract #2080, published in Circulation (1997), 1 page.
Hassanein, W.H. et al., "Continuous Perfusion of Donor Hearts in the Beating State Extends Preservation Time and Improves Recovery of Function", The Journal of Thoracic and Cardiovascular Surgery, pp. 821-830 (1998), 10 pages.
Heil, J.E. et al., "A Controlled Comparison of Kidney Preservation by Two Methods: Machine Perfusion and Cold Storage", Transplantation Proceedings 19(1):2046 (1987), 1 page.
Howarth, F.C. et al., "Effects of extracellular magnesium and beta adrenergic stimulation on contractile force and magnesium mobilization in the isolated rat heart", Magnesium Research, 7:187-197, 1994 (13 pages).
Synchrony Definition, http://dictionary.reference.com/browse/synchrony, Random House Unabridged Dictionary, 2006 (1 page).
Hülsmann, W.C. et al., "Loss of cardiac contractility and severe morphologic changes by acutely lowering the pH of the perfusion medium: protection by fatty acids", BBAGEN 20256, Biochimica et Biophysica Acta., 1033:214-218 (1990) (5 pages).
Imber, C. J. et al., "Advantages of Normothermic Perfusion Over Cold Storage in Liver Preservation", Transplantation, 73(5):701-709 (2002), 9 pages.

International Search Report and Written Opinion, issued by the U.S. Patent and Trademark Office as Searching Authority, for International Application No. PCT/US2012/033626 dated Sep. 20, 2012 (12 pages).
Janßen, H. et al., "UW is Superior to Celsior and HTK in the Protection of Human Liver Endothelial Cells Against Preservation Injury", Liver Transplantation, 10(12):1514-1523 (2004), 10 pages.
Johnson, Kerry et al, "POPS: Portable Organ Preservation System", UPMC Health System and TransMedics, Inc. (No date) (1 page).
Johnston, R., "What's Normal About DLCO?", PFT Blog, Jan. 1, 2014 (17 pages).
Semat, H. et al.,"Physics, Chapter 9: Hydrodynamics (Fluids in Motion)", Hydrodynamics. University of Nebraska—Lincoln. Pap143. Jan. 1, 1958 (18 pages).
Kawamura, T. et al., "Long-Term Preservation of Canine Pancreas by a New Simple Cold Storage Method Using Perfluorochemical— The Two-Layer Cold Storage Method (Euro-Collins' Solution/Perfluorochemical)—", Kobe J. Med. Sci., 38(2):135-145 (1992), 11 pages.
Kelly, R.F., "Current strategies in lung preservation", J. Lab Clin Med, 136:427-440 (Dec. 2000), 14 pages.
Keshavjee, S.H. et al., "A method for safe twelve-hour pulmonary preservation", J Thorac Cardiovasc Surg, 98:529-534 (1989), 6 pages.
Kioka, Y. et al., "Twenty-Four-Hour Isolated Heart Preservation by Perfusion Method With Oxygenated Solution Containing Perfluorochemicals and Albumin", The Journal of Heart Transplantation, 5(6):437-443 (1986), (Nov./Dec. 1986), 7 pages.
Kozaki, K. et al., "Usefulness of a Combination of Machine Perfusion and Pentoxifylline for Porcine Liver Transplantation From Non-Heart-Beating Donors With Prolonged Hypotension", Transplantation Proceedings, 29:3476-3477 (1997), 2 pages.
Kuroda, Y. et al., "A New, Simple Method for Cold Storage of the Pancreas Using Perfluorochemical", Transplantation, 46(3):457-460 (Sep. 1988), 4 pages.
Lasley, R.D. et al., "Protective Effects of Adenosine in the Reversibly Injured Heart", Ann Thorac Surg, 60(3):843-846 (1995), 4 pages.
Lawrence, C., "Machine preserves organs outside body," Chicago Sun Times (Nov. 4, 2001), 1 page.
Lefer, A.M., "Attenuation of Myocardial Ischemia-Reperfusion Injury With Nitric Oxide Replacement Therapy", Ann Thorac Surg 60(3):847-851 (1995), 5 pages.
Li, G. et al., "Functional Recovery in Rabbit Heart after Preservation with a Blood Cardioplegic Solution and Perfusion," J Heart Lung Transplant, 12(2)263-270 (1993) (8 pages).
Li, X. et al., "Insulin in University of Wisconsin Solution Exacerbates the Ischemic Injury and Decreases the Graft Survival Rate in Rat Liver Transplantation", Transplantation, 15:76(1):44-49 (Jul. 15, 2003), 6 pages.
Li, X. et al., "Insulin in UW Solution Exacerbates Hepatic Ischemia / Reperfusion Injury by Energy Depletion Through the IRS-2 / SREBP—1c Pathway", Liver Transplantation, 10(9):1173-1182 (Sep. 2004), 10 pages.
Liu,J. et al., "Annexin V Assay-proven Anti-apoptotic Effect of Ascorbic Acid 2-glucoside after Cold Ischemia/Reperfusion Injury in Rat Liver Transplantation", Acta Med. Okayama, 57(5):209-216 (2003), 8 pages.
Macchiarini, P. et al. "Ex Vivo Lung Model of Pig-To-Human Hyperacute Xenograft Rejection", The Journal of Thoracic and Cardiovascular Surgery, 114(3): 315-325 (Sep. 1997) (11 pages).
Mankad, P. et al., "Endothelial dysfunction caused by University of Wisconsin preservation solution in the rat heart", J Thorac Cardiovasc Surg 104(6): 1618-1624 (Dec. 1992), 7 pages.
Matsuno, N. et al., "Effectiveness of Machine Perfusion Preservation as a Viability Determination Method for Kidneys Procured from Non-Heart-Beating Donors," Transplantation Proceedings, 26(4):2421-2422 (Aug. 1994) (2 pages).
Matsuno, N. et al., "The Effect of Machine Perfusion Preservation Versus Cold Storage on the Function of Kidneys From Non-Heart-Beating Donors", Transplantation, 57(2):293-294 (Jan. 1994) (2 pages).

(56) References Cited

OTHER PUBLICATIONS

Menasché, P. et al., "Experimental evaluation of Celsior®, a new heart preservation solution," Eur J Cardio-thorac Surg 8:207-213 (1994), 7 pages.
Menasché, P. et al., "Improved recovery of heart transplants with a specific kit of preservation solutions," The Journal of Thoracic and Cardiovascular Surgery, 105(2):353-363 (Feb. 1993), 11 pages.
Menasché, P., "The inflammatory response to cardiopulmonary bypass and its impact on postoperative myocardial function", Current Opinion in Cardiology, 10:597-604 (1995) (8 pages).
Moisiuk, Y. et al., "Histidine-Tryptophan-Ketoglutarate Versus Euro-Collins for Preservation of Kidneys From Non-Heart-Beating Donors", Transplantation Proceedings, 28(1):202 (Feb. 1996) (1 page).
Moller-Pedersen, T. et al., "Evaluation of potential organ culture media for eye banking using human donor corneas", Br J Ophthalmol, 85(9):1075-1079 (2001), 5 pages.
Morimoto, T. et al., "A Simple Method for Extended Heart-Lung Preservation by Autoperfusion", Trans Am Soc Artif Intern Organs, 30:320-324 (1984), 5 pages.
Nicholson, M.L. et al., "A Comparison of Renal Preservation by Cold Storage and Machine Perfusion Using a Porcine Autotransplant Model", Transplantation 78(3):333-337 (Aug. 15, 2004), 5 pages.
No Author Listed, "CUSTODIOL® HTK Solution for Multi-Organ Protection", Saudi Center for Organ Transplantation, Date Unknown (2 pages).
No Author Listed, "SOLTRAN Kidney perfusion fluid", Baxter, No Month Listed—2001-2004 (1 page).
No Author Listed, "The comprehensive resource for physicians, drug and illness information", VIASPAN™ DuPont Pharma Cold Storage Solution, Date Unknown (3 pages).
No Author Listed, "UW Solution Composition", DuPont Pharmaceuticals, Date Unknown (1 page).
No Author Listed, "Custodiol HTK" Physicians' Desk Reference, 57th Edition, Thomson PDR. ISBN:1-5636-445-7. No Month Listed—2003 (3 pages).
Odagiri, S. et al., "Pusatile Assist Device: New Pulsatile Pump Using Pulsatile Assist Device—Hemodynamic Comparison of Pulsatile V-A Bypass (VABP), Pulsatile Left Heart Bypass (LHBP) and Constant Flow Left Heart Bypass (LHB)", Journal of Japan Surgical Society, 83(6):515-523, Jun. 1982, 12 pages—English Abstract.
Opelz, G. et al., "Advantage of Cold Storage Over Machine Perfusion for Preservation of Cadaver Kidneys", Transplantation, 33(1):64-68 (Jan. 1982), 5 pages.
Opelz, G. et al., "Comparative Analysis of Kidney Preservation Methods", Transplantation Proceedings 28(1):87-90 (Feb. 1996), 4 pages.
Ota, K. et al., "Artificial Organ", Current State and Future of Substitution of Functions, pp. 150-151, 1983 (7 pages)—English Translation.
International Search Report, issued by the European Patent Office as Searching Authority, issued in PCT/US07/009652, dated Apr. 18, 2008, 5 pages.
International Search Report, issued by the U.S. Patent Office as Searching Authority, issued in PCT/US08/61454, dated Dec. 5, 2008 (3 pages).
International Search Report, issued by the U.S. Patent Office as Searching Authority, issued in PCT/US09/032619, dated Jun. 4, 2009 (4 pages).
International Search Report, issued by the European Patent Office as Searching Authority, issued in PCT/US 98/19912, dated Mar. 5, 1999 (4 pages).
Pearl, J.M. et al., "Loss of endothelium-dependent vasodilatation and nitric oxide release after myocardial protection with University of Wisconsin solution", Journal of Thoracic Cardiovascular Surgery 107(1):257-264 (Jan. 1994) (8 pages).
Petrovsky, B.V. et al., "Justification and Application of a New Method for Transorganic Oxygen Preservation of the Kidneys", Vestn. Akad. Med. Nauk, USSR., (2):69-82 (1989)—English Abstract, 15 pages.

Pinsky, D. et al., "Restoration of the cAMP Second Messenger Pathway Enhances Cardiac Preservation for Transplantation in a Heterotopic Rat Model", J. Clin. Invest. 92(6):2994-3002 (Dec. 1993) (9 pages).
Ploeg, R.J. et al., "Successful 72-Hour Cold Storage of Dog Kidneys With UW Solution", Transplantation, 46(2):191-196 (Aug. 1988), 6 pages.
Pokorny, H. et al., "Histidine-tryptophan-ketoglutarate solution for organ preservation in human liver transplantation—a prospective multi-centre observation study", Transpl Int 17(5):256-260 (2004), (5 pages).
Poston, R.S. et al., "Optimizing Donor Heart Outcome After Prolonged Storage With Endothelial Function Analysis and Continuous Perfusion", Ann Thorac Surg, 78:1362-1370, 2004 (9 pages).
Potdar, S. et al., "Initial experience using histidine-tryptophan-ketoglutarate solution in clinical pancreas transplantation", Clin Transplant, 18(6):661-665 (2004), 5 pages.
Pozniak, A., "Keeping Hearts Alive Doctors Develop a High-Tech System to Salvage Donated Organs", ABC News.com (Dec. 7, 2001) (2 pages).
Probst, I. et al. "Carbohydrate and fatty acid metabolism of cultured adult cardiac myocytes", Am. J. Physiol. 250 (Heart, Circ. Physiol. 19):H853-H860 (1986) (8 pages).
Rao, V. et al., "Donor Blood Perfusion Improves Myocardial Recovery After Heart Transplantation", J. Heart Lung Transplant. 16(6):667-673 (Jun. 1997) (7 pages).
Reddy, S.P. et al., "Preservation of Porcine Non-Heart-Beating Donor Livers by Sequential Cold Storage and Warm Perfusion", Transplantation, 77(9):1328-1332 (May 15, 2004), 5 pages.
Richens, D. et al., "Clinical Study of Crystalloid Cardioplegia vs Aspartate-Enriched Cardioplegia Plus Warm Reperfusion for Donor Heart Preservation", Transplantation Proceedings 25(1): 1608-1610 (Feb. 1993) (3 pages).
Rinder, C.S. et al., "Blockade of C5a and C5b-9 Generation Inhibits Leukocyte and Platelet Activation during Extracorporeal Circulation", J. Clin. Invest. 96:3(1564-1572), Sep. 1995 (9 pages).
Rosenkranz, E.R., "Substrate Enhancement of Cardioplegic Solution: Experimental Studies and Clinical Evaluation", Ann Thorac Surg 60:797-800 (1995) (4 pages).
Rossi, L. et al., "Innovations-report: New organ preservation solution easier to use", Feb. 6, 2003, printed Jul. 21, 2006 (2 pages).
Rossi, L., "Portable Organ Preservation System™ Keeps Human Heart Alive Outside Body", PITT Campaign Chronicle (2001), 2 pages.
Sato, H. et al., "Supplemental $_L$-Arginine During Cardioplegic Arrest and Reperfusion Avoids Regional Postischemic Injury", J Thorac Cardiovasc Surg 110(2):302-314 (Aug. 1995), 13 pages.
Schmid, T. et al., "The Use of Myocytes as a Model for Developing Successful Heart Preservation Solutions", Transplantation 52(1):20-26 (Jul. 1991) (7 pages).
Schon, M.R. et al., "Liver Transplantation After Organ Preservation With Normothermic Extracorporeal Perfusion", Annals of Surgery 233(1):114-123 (Jan. 2001), 10 pages.
Schwalb, H. et al., "New Solution for Prolonged Myocardial Preservation for Transplantation", The Journal of Heart and Lung Transplantation 17(2):222-229 (Feb. 1998), 8 pages.
Seccombe, J.F. et al., "Coronary Artery Endothelial Function After Myocardial Ischemia and Reperfusion", Ann Thorac Surg 60(3):778-788 (1995), 11 pages.
Segel, L.D. et al., "Posttransplantation Function of Hearts Preserved with Fluorochemical Emulsion", J Heart Lung Transplant, 13(4):669-680 (Jul./Aug. 1994), 12 pages.
Segel, L.D. et al., "Recovery of Sheep Hearts After Perfusion Preservation or Static Storage with Crystalloid Media", The Journal of Heart and Lung Transplantation, 17(2):211-221 (Feb. 1998) (11 pages).
Shimokawa, S. et al., "A New Lung Preservation Method of Topical Cooling by Ambient Cold Air Combined with High-Frequency Oscillation: An Experimental Study", Transplantation Proceedings, 26(4):2364-2366 (Aug. 1994) (3 pages).
Shimokawa, S. et al., "A New Lung Preservation Method of Topical Cooling by Ambient Cold Air: An Experimental Study", Transplantation Proceedings, 23(1):653-654 (Feb. 1991) (2 pages).

(56) References Cited

OTHER PUBLICATIONS

Shirakura, R. et al., "Multiorgan Procurement from Non-Heart-Beating Donors by use of Osaka University Cocktail, Osaka Rinse Solution, and the Portable Cardiopulmonary Bypass Machine", Transplantation Proceedings, 25(6):3093-3094 (Dec. 1993) (2 pages).
Southard, J., "The Right Solution for Organ Preservation", Business Briefings: Global Surgery 79-84 (2004) (6 pages).
Steen, S. et al., "Transplantation of lungs from non-heart-beating donors after functional assessment ex vivo", Ann Thorac Surg, 76:244-252, 2003, printed Jan. 22, 2007, 11 pages.
Stubenitsky, B.M. et al., "Kidney preservation in the next millenium", Transpl Int, 12:83-91 (1999), 9 pages.
Sunamori, M. et al., "Relative Advantages of Nondepolarizing Solution to Depolarizing University of Wisconsin Solution in Donor Heart Preservation", Transplantation Proceedings, 25(1):1613-1617 (Feb. 1993), 5 pages.
Tang, D.G. et al., "Warm Ischemia Lung Protection With Pinacidil: An ATP Regulated Potassium Channel Opener", Ann Thorac Surg, 76:385-90 (2003), 6 pages.
Tesi, R.J. et al., "Pulsatile Kidney Perfusion for Preservation and Evaluation: Use of High-Risk Kidney Donors to Expand the Donor Pool", Transplantation Proceedings, 25(6):3099-3100 (Dec. 1993) (2 pages).
Turpin, B.P. et al., "Perifusion of Isolated Rat Adipose Cells", The Journal of Clinical Investigation, 60:442-448 (Aug. 1977), 7 pages.
U.S. Food and Drug Administration, Center for Drug Evaluation and Research, "Drugs@FDA—Solu-Medrol: Label and Approval History", NDA 011856, (Available online at http://www.accessdata.fda.gov/scripts/cder/drugsatfda/index.cfm?fuseaction=Search.Label_ApprovalHistory#apphist . . . ), accessed Feb. 9, 2010 (3 pages).
U.S. Food and Drug Administration, Center for Drug Evaluation and Research, "Drugs@FDA—Solu-Medrol: Drug Details", NDA 011856, (Accessible online at http://www.accessdata.fda.gov/scripts/cder/drugsatfda/index.cfm?fuseaction=Search.DrugDetails . . . ), accessed Feb. 9, 2010 (1 page).
Vinten-Johansen, J. et al., "Reduction in Surgical Ischemic-Reperfusion Injury With Adenosine and Nitric Oxide Therapy", Ann Thorac Surg 60(3):852-857 (1995), 6 pages.
Voiglio, E. J. et al. "Rat Multiple Organ Blocks: Microsurgical Technique of Removal for Ex Vivo Aerobic Organ Preservation Using a Fluorocarbon Emulsion", Microsurgery 20(3):109-115 (2000) (7 pages).
Watanabe, S. et al., "Effects of free fatty acids on the binding of bovine and human serum albumin with steroid hormones", Biochimica et Biophysica Acta (BBA), 1289:385-396 (1996), 12 pages.
Wei, Z. et al., "A Study on the Preservation of Rat Kidney with HX-III Solution", J WCUMS, 31(3):347-349 (2000)—English Abstract, 5 pages.
Wicomb, W. et al., "Orthotopic transplantation of the baboon heart after 20 to 24 hours' preservation by continuous hypothermic perfusion with an oxygenated hyperosmolar solution", J Thorac Cardiovasc Surg, 83(1):133-140 (Jan. 1982), 8 pages.
Wicomb, W.N. et al., "24-Hour Rabbit Heart Storage With UW Solution", Transplantation, 48(1):6-9 (Jul. 1989), 4 pages.
Wicomb, W.N. et al., "Cardiac Transplantation Following Storage of the Donor Heart by a Portable Hypothermic Perfusion System", The Annals of Thoracic Surgery, 37(3):243-248 (Mar. 1984), 6 pages.
Wright, N. C. et al. "A porcine ex vivo paracorporeal model of lung transplantation", Laboratory Animals Ltd. Laboratory Animals, 34:1, 56-62 (2000) (7 pages).
Yeung, J. C., et al., "Physiologic assessment of the ex vivo donor lung for transplantation", The Journal of Heart and Lung Transplantation, 31(10):1120-1126, Oct. 2012 (7 pages).
Yland, M.J. et al., "New Pulsatile Perfusion Method for Non-Heart-Beating Cadaveric Donor Organs: A Preliminary Report", Transplantation Proceedings, 25(6):3087-3090 (Dec. 1993), 4 pages.
Zhang, Z. et al., "Research Progress on Preservation of Severed Limbs", Chinese Journal of Reparative and Reconstructive Surgery, 14(3):189-192 (2000)—English Abstract, 8 pages.
Chinchoy, Edward Cheng-wey; "The Development, Refinement, and Uses of a Physiologically Working Isolated Ex Vivo Swine Heart Model", Thesis submitted to the Faculty of the Graduate School of the University of Minnesota, Dec. 1999 (136 pages).
International Search Report and Written Opinion issued by the U.S. Patent and Trademark Office as Searching Authority, in International Application No. PCT/US16/50512, dated Dec. 12, 2016 (9 pages).
Extended European Search Report issued in European Application No. 17172411.5, dated Nov. 8, 2017 (7 pages).
Kubono, K. et al., "Examination of Plasma and Corpuscle Adenosine Concentration in Normal Subject by Radioimmunoassay", Rinshou Kagaku (Clinical Chemistry, 20(2):72-77, Jun. 1991 (6 pages)—Japanese Language.
Sekine, M. et al., "Effect of Obese and Aging on Blood Fatty Acid Consumption in Japanese", Bulletin of the Graduate School of Human Life Science, Showa Women's University, 4:63-70, 1995 (8 pages)—English Abstract.
Yokoyama, H. et al., "Isolated Dog Hearts Prepared in Cold Tyrode Solution and Reperfused with Arterial Blood Are Functionally and Ultrastructurally Normal", The Tohoku Journal of Experimental Medicine, 156:121-134, 1988 (14 pages).
Botha, P., "Extended Donor Criteria in Lung Transplantation", Current Opinion in Organ Transplantation, 14:206-210, 2009 (5 pages).
Extended European Search Report issued in EP15803127.8, dated May 22, 2018 (14 pages).
Kawakami, et al., "Successful Preservation of the Isolated Canine Heart for 24 Hours by Low Pressure-Low Temperature Continuous Perfusion", Japanese Annals of Thoracic Surgery, Japan, 7(6):543-547, Dec. 25, 1987 (13 pages)—English Translation.
Koike, et al., "An Experimental Study on the Hypothermic Preservation of the Rabbit Heart Using Glucose-Insulin-Potassium Solution—Intermittent Perfusion Method Versus Simple Immersion Method", Japanese Annals of Thoracic Surgery, 7(6):527-532, Dec. 25, 1987 (16 pages)—English Translation.

* cited by examiner

AORTIC CANNULA FOR EX VIVO ORGAN CARE SYSTEM

RELATED APPLICATIONS

This application is related to Application Ser. No. 62/215,825, titled "Aortic Cannula for Ex Vivo Organ Care System," filed Sep. 9, 2015, which is incorporated herein by reference in its entirety.

TECHNICAL FIELD

The present invention relates generally to medical devices and, in particular, aortic cannulas for use in ex vivo organ care systems. Specifically the invention relates to aortic cannulas used to return perfusate to the heart or delivering perfusate from the heart while the organ is sustained ex vivo at physiologic or near-physiologic conditions.

BACKGROUND

Current organ preservation techniques typically involve hypothermic storage of the organ in a chemical perfusate solution on ice. However, uses of conventional approaches results in injuries that increase as a function of the length of time an organ is maintained ex-vivo. These time restrictions limit the number of recipients who can be reached from a given donor site, thereby restricting the recipient pool for a harvested heart. Even within the few hour time limit, the heart may nevertheless be significantly damaged.

Effective preservation of an ex-vivo organ would also provide numerous other benefits. For instance, prolonged ex-vivo preservation would permit more careful monitoring and functional testing of the harvested organ. This would in turn allow earlier detection and potential repair of defects in the harvested organ, further reducing the likelihood of transplantation failure. The ability to perform simple repairs on the organ would also allow many organs with minor defects to be saved, whereas current transplantation techniques require them to be discarded. In addition, more effective matching between the organ and a particular recipient may be achieved, further reducing the likelihood of eventual organ rejection.

Improved ex-vivo organ care has been achieved through the use of an ex-vivo organ care system which maintains organs at physiologic or near-physiologic conditions. Not only does the system maintain the organ at physiologic temperatures, but in the case of the heart, the system maintains perfusate flow through the organ. In addition the system measures and monitors electric stimulation in the heart. The ex vivo organ care system where the heart sustained ex vivo at physiologic or near-physiologic conditions are described in application Ser. No. 11/822,495 entitled "Systems for monitoring and applying electrical currents in an organ perfusion system," U.S. Pat. No. 8,304,181 entitled "Method for ex-vivo organ care and for using lactate as an indication of donor organ status," and U.S. Pat. No. 8,409,846 entitled "Compositions, methods and devices for maintaining an organ," which are incorporated herein by reference.

To maintain physiologic or near-physiologic perfusate flow through the heart, the organ must interface with the system via the aorta. This interface is achieved via an aortic cannula. Current aortic cannula designs lead to organ slippage, difficulties in maintaining a liquid tight seal, and damage to the aorta. Often these designs rely solely upon a cable tie in contact with the aorta to tighten the aorta to the aortic cannula. Depending on the size of the aorta and the size of the aortic cannula, there is a risk of laceration due to the cable ties exerting too much tension on aortic tissue, or the risk of leakage if they do not exert sufficient tension. Thus, there exists a need for an aortic cannula that is easy for health care workers to deploy, creates a tight seal with the aorta, reduces aortic slipping, and causes minimal damage to the aorta.

In view of the foregoing, improved devices for attaching the aorta to the system and methods of use in ex vivo organ care systems are needed.

SUMMARY

In one embodiment the invention includes an aortic cannula for use with an ex vivo organ care system and methods of using the same. One aspect of the invention includes an aortic cannula comprising, a cannula body which further comprises, a fitting adapted to connect to an organ care system, an aorta interface to contact an aorta, and a pivot arm strap operably connected to a pivot mount, wherein the pivot mount allows the pivot arm strap to uniformly contact the aorta to hold the aorta on the aorta interface. In one embodiment, the aortic cannula further comprises a pivot arm connected to the pivot arm strap and to the pivot mount, such that when the pivot arm is moved toward the cannula body by rotation around the pivot mount the pivot arm strap moves away from the cannula body. In another embodiment of the aortic cannula the pivot arm and the pivot arm strap are parts of a single piece. In another embodiment, the aortic cannula comprises a spring which applies pressure to the pivot arm strap to hold the aorta on the aorta interface. In another embodiment of the aortic cannula a dowel pin communicates with the spring to allow the pivot arm to rotate around the dowel pin. In another embodiment of the aortic cannula the pivot arm further comprises a grip pad used to depress the top of the pivot arm. In another embodiment of the aortic cannula the grip pad is textured. In another embodiment of the aortic cannula the grip pad is removable. In another embodiment of the aortic cannula the pivot arm straps further comprise a loop and guide which retain a cable tie around the pivot arm strap. In another embodiment, the aortic cannula further comprises windows sized to normalize the compression exerted on the aorta by the cable tie such that the same amount of pressure will be exerted on the aorta regardless of the size of the pivot arm strap for a given cable tie tension. In another embodiment, the aortic cannula further comprises a connector used to reversibly secure the aortic cannula to an organ chamber. In another embodiment of the aortic cannula the connector is a threaded locking nut. In another embodiment of the aortic cannula the aorta interface is textured.

One aspect of the invention includes a method of using an aortic cannula to place a heart in fluid communication with an organ care system the method comprising, selecting an aortic cannula sized to fit the aorta of the heart the aortic cannula comprising, a cannula body further comprising, a fitting adapted to connect to an organ care system, an aorta interface to contact an aorta, and a pivot arm strap operably connected to a pivot mount, wherein the pivot mount allows the pivot arm strap to uniformly contact the aorta to hold the aorta on the aorta interface, depressing the pivot arm such that it rotates around the dowel pin and the pivot arm strap moves away from the cannula body, placing the cannula in the aorta, releasing the pivot arm, tightening a cable tie around the pivot arm strap to hold the aorta in place, and inserting the tapered fitting into an organ care system. In one embodiment, the method further comprises the step of suturing surgical felt pledgets on the aorta before placing the aorta on the aortic cannula.

BRIEF DESCRIPTION OF THE FIGURES

The following figures depict illustrative embodiments of the invention.

DETAILED DESCRIPTION

Cannula Body

Figure 1:
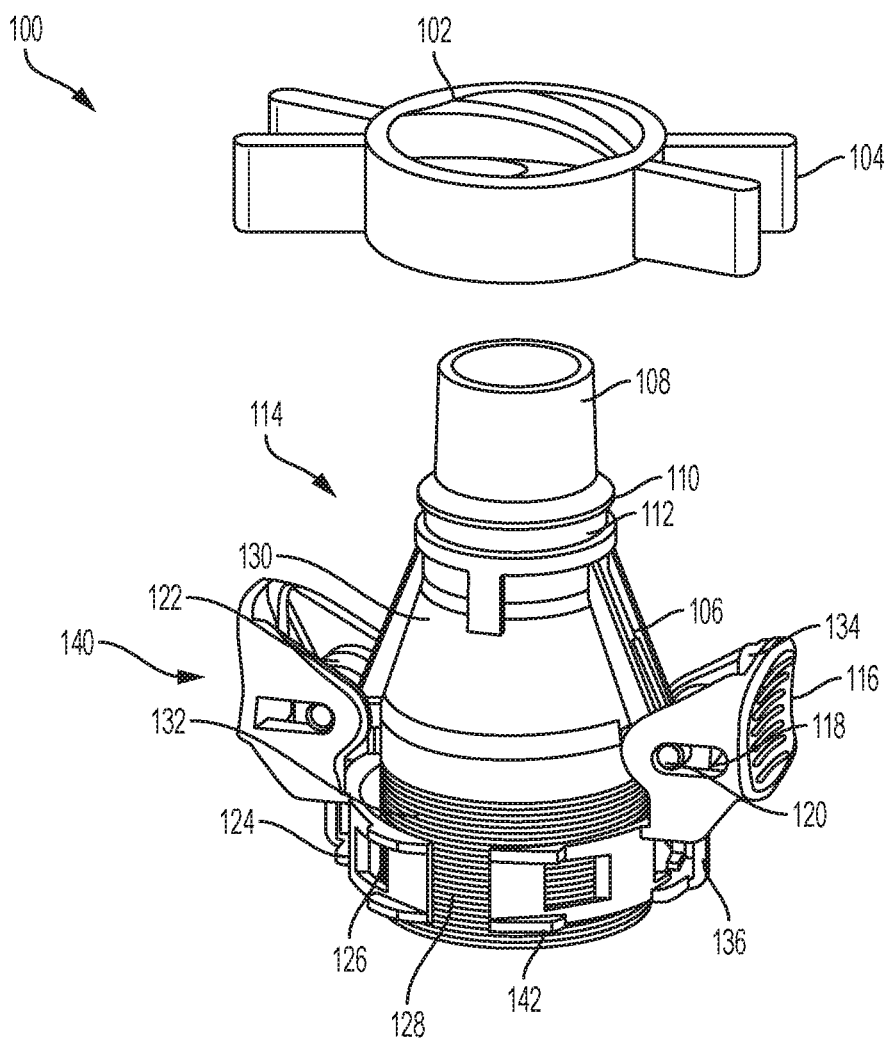
FIG. 1 illustrates a diagram depicting an aortic cannula in one embodiment.
Figure 2A:
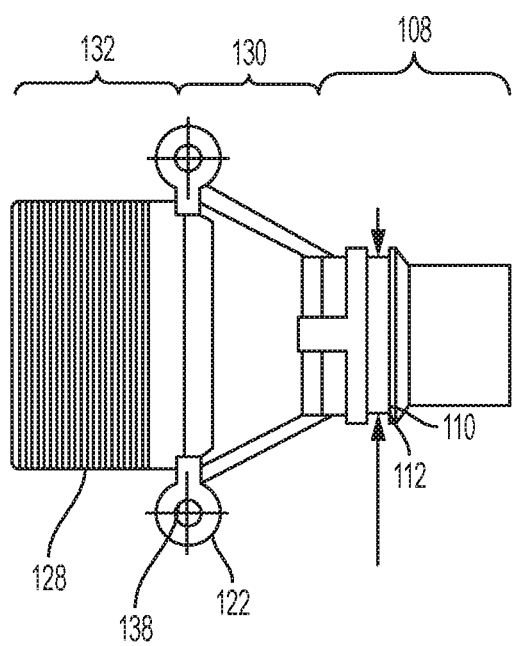
FIG. 2a illustrates a side view of a cannula body in one embodiment.
Figure 2B:
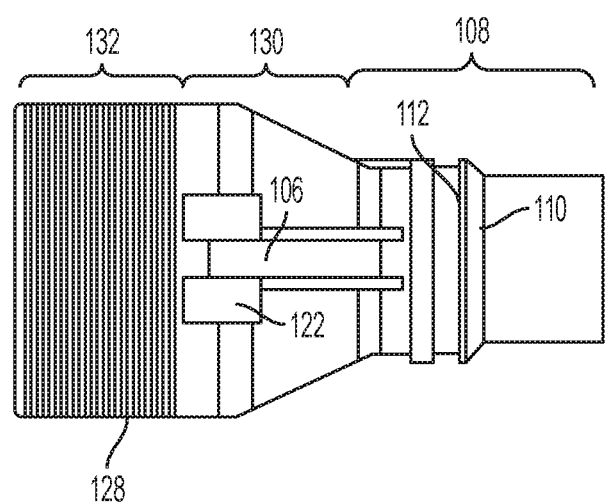
FIG. 2b illustrates a side view of a cannula body and a spring pocket according to one embodiment.
Figure 2C:
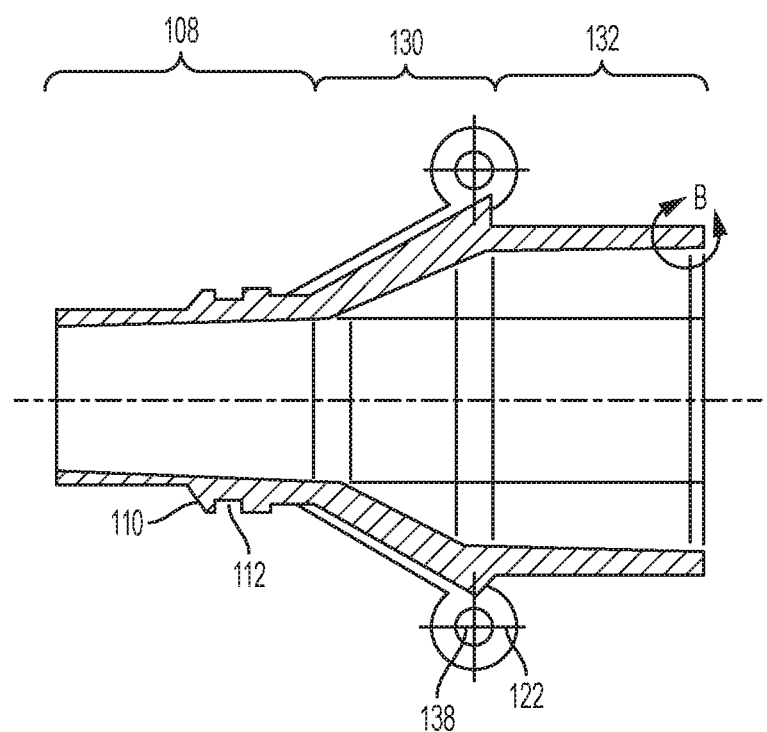
FIG. 2c illustrates a side view of a cannula body in one embodiment.

FIG. 1 is a diagram depicting the aortic cannula 100 in one embodiment. The aortic cannula device 100 comprises a cannula body 114, a locking nut 102, and a pivot arm 140. The cannula body 114 may contain three sub-sections, a tapered fitting 108, a tapered midsection 130 and an aorta interface 132. These subsections can be seen in FIG. 1 as well as in various side views of the cannula body 114 depicted in FIGS. 2a-2b. In one embodiment, the cannula body 114 is made from injection molded clear polycarbonate. However, one of skill in the art would understand that the cannula body can be made from other types of plastic or any other suitable material.

One of skill in the art would recognize that the while the shape of the cannula body 114 should be generally cylindrical, the opening need not be perfectly circular. The three sub-sections, tapered fitting 108, tapered midsection 130, and aorta interface 132, may be of different lengths relative to one another. In addition the different subsections may be made from one piece and they may have the same diameter. One of skill in the art would also recognize that the taper angle in the sub-sections, tapered fitting 108, tapered midsection 130, and aorta interface 132, may vary so long as the aorta interface reaches a diameter within the typical range of the diameter of an human aorta.

One end of the aortic cannula 100 forms tapered fitting 108. The tapered fitting is sized to couple to a female connector on an organ chamber (not shown) to create a seal. A threaded locking nut 102, pictured in FIG. 1, is used to reversibly secure the aortic cannula 100 to the organ chamber (not shown). In one embodiment, the locking nut 102 has four wings 104 extending from its outer surface that are used for gripping and turning the locking nut 102 in one embodiment the wings 104 are rectangular. One of skill in the art would understand that the wings 104 could be any shape or omitted. The locking nut 102 may have a lip protruding inward from its bottom edge that snaps over locking ridge 110 and into the locking groove 112 on the cannula body 114. The locking groove 112 and the locking ridge 110 can be seen in FIG. 1 and FIGS. 2a-2b. Alternatively, the locking nut 102 may be secured to the cannula body 114 using other mechanisms known to one skilled in the art. Once the locking nut 102 is seated in the locking groove 112, the aortic cannula 100 is securely fastened to the organ chamber (not shown) by turning the locking nut 102. Perfusate can be perfused through the cannula into the heart without leaking. One of skill in the art would understand that other designs can be used to attach the aortic cannula 100 to the organ chamber to prevent leakage.

One of skill in the art would understand that the aortic cannula 100 can be connected to an organ care system or any other tube, device, or path of flow. In addition, one of skill in the art would appreciate that the locking nut 102 may be omitted in embodiments where the male-female connection between the aortic cannula 100 and the organ care system (not shown) is tight enough to prevent leakage. One of skill in the art would also recognize that the locking nut 102 could be replaced with other types of connectors generally used in the art to create a flow path between two tubes.

Figure 3A:
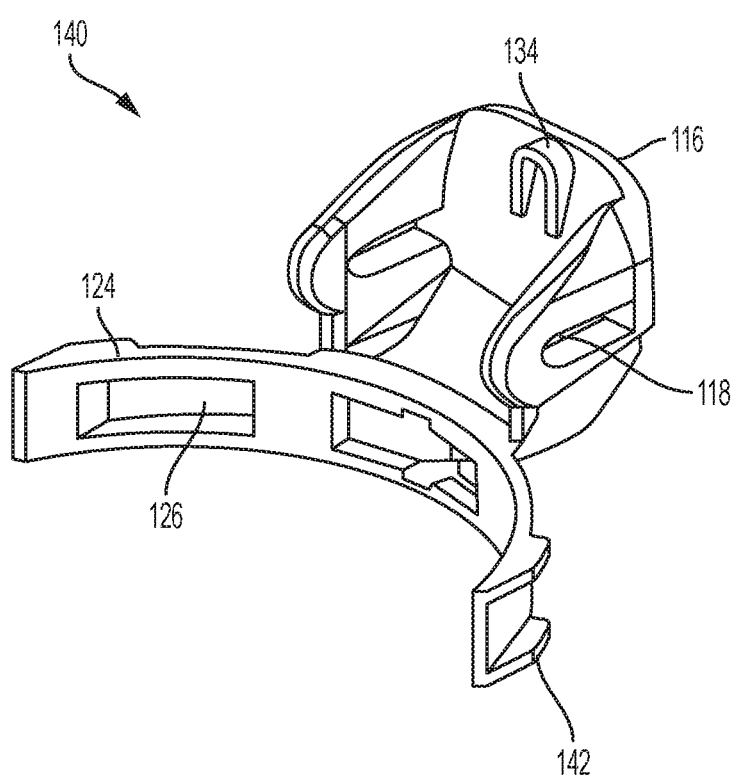
FIG. 3a illustrates one embodiment of a pivot arm.
Figure 3B:
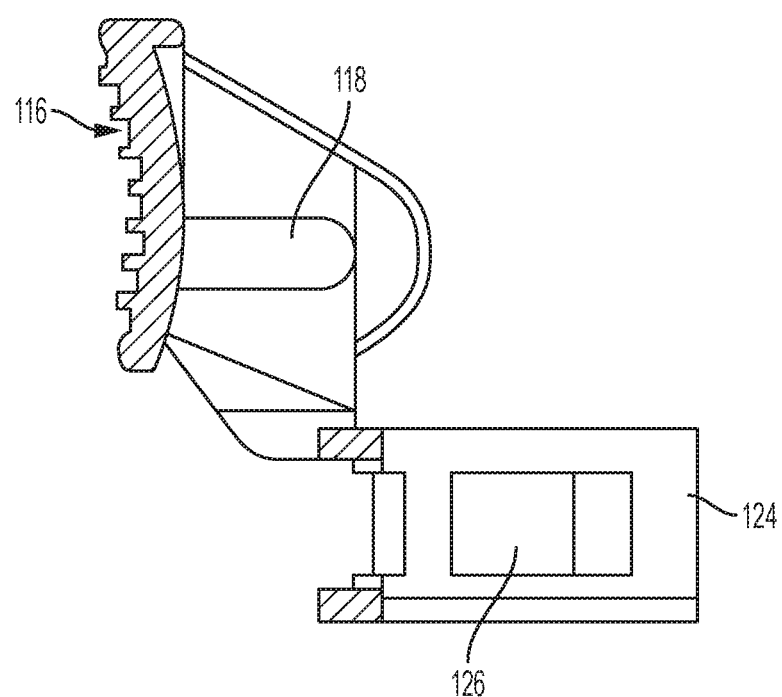
FIG. 3b illustrates a side view of a pivot arm and strap according to one embodiment.
Figure 3C:
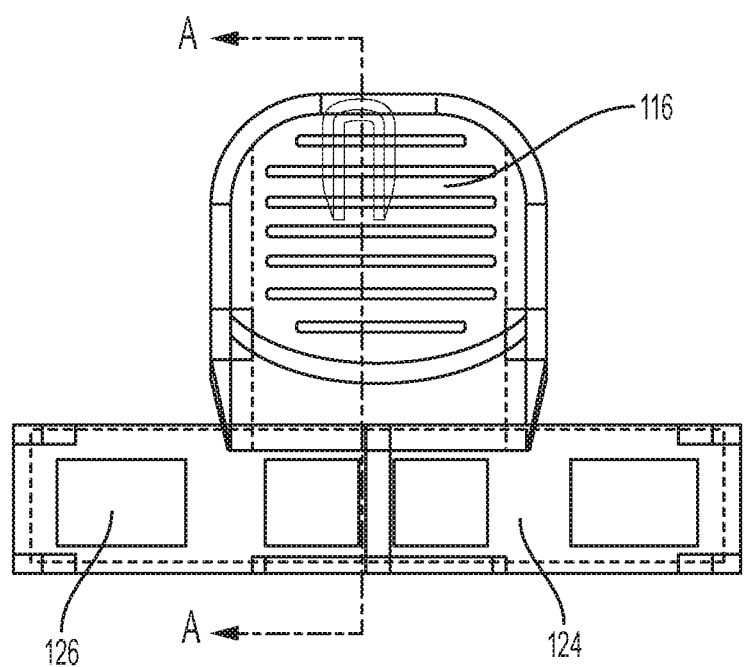
FIG. 3c illustrates another view of a pivot arm and strap according to one embodiment.
Figure 3D:
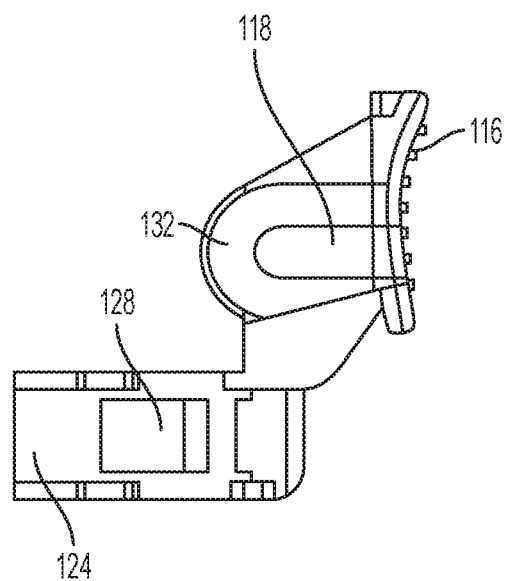
FIG. 3d illustrates another view of a pivot arm and strap according to one embodiment.
Figure 3E:
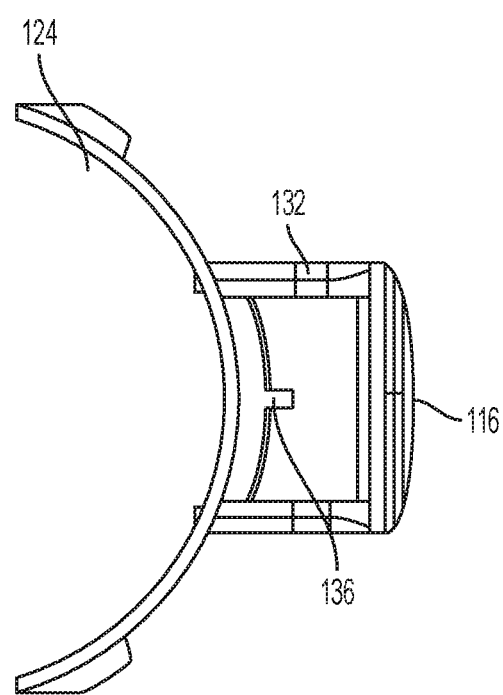
FIG. 3e illustrates a top view of a pivot arm and strap according to one embodiment.
Figure 5:
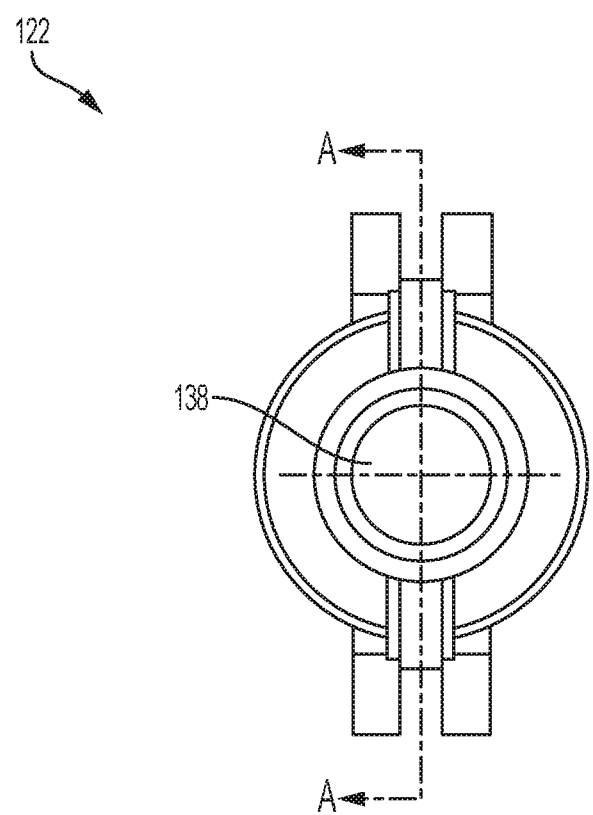
FIG. 5 illustrates a top view of a pivot mount according to one embodiment.

The tapered midsection 130 extends from the bottom edge of the tapered fitting 108 to the top edge of the aorta interface 132. The tapered midsection 130 reaches a final diameter the size of the aorta interface 132. The tapered midsection 130 helps to ensure smooth fluid flow from the aorta interface 132 to the tapered fitting 108. The tapered midsection 130 also helps minimize air trap and hemolysis and improve hemodynamics due to the smooth transition in flow path. The tapered midsection 130 has a pivot mount 122 and a spring pocket 106. The pivot mount 122 and the spring pocket 106 may be integrated with the tapered midsection 130. In one embodiment, the tapered midsection 130 has two pivot mounts 122 and two spring pockets 106, shown in FIGS. 1 and 2b. The pivot mounts 122 are located on each side of the cannula body 114. One of ordinary skill in the art would understand that one or more pivot mounts 122 and spring pockets 106 could be used. As shown in FIG. 5, in one embodiment the pivot mount 122 has a circular center hole 138 sized to receive a dowel pin 120. The spring pocket 106 is located on the cannula body 114 and provides a space for a torsional spring (not shown). The dowel pin 120 fits through one side of the center hole 138 on the integrated pivot mount 122, through the center of the torsional spring in the spring pocket 106, and through the other side of the center hole 138 on the integrated pivot mount 122. The torsional spring is oriented in spring pocket 106 such that depressing the pivot arm compresses the spring. One end of the torsional spring rests in the spring end pocket 134 on the thumb pad 116 seen in FIG. 3a. One of ordinary skill in the art would understand that there are various ways to attach the pivot mount 122 to the cannula body 114 that allows the pivot mount 122 to pivot or move so that the aorta can be fit onto the cannula body 114 in operation. In one embodiment, the pivot mount 122 is made from injection molded polycarbonate, acetyl, or any suitable material.

One of skill in the art would also recognize that the torsional spring could be replaced with other types of spring loading mechanisms or omitted completely. The torsional spring could also be replaced by a molded leaf spring on the pivot arm or on the grip pad. With the use of a molded leaf spring the dowel pin would be omitted and cylindrical bosses on the cannula body 114 or a similar structure could be used to perform the same function.

Figure 4:
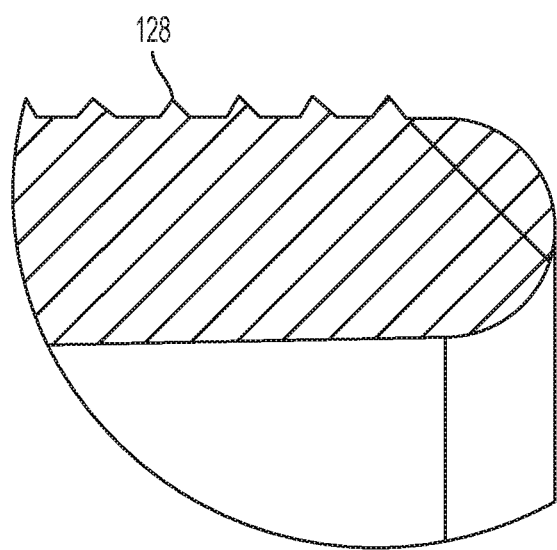
FIG. 4 illustrates a diagram showing the shape of a cannula body texture in one embodiment.

The aorta interface 132 is located adjacent the tapered midsection 130. The aorta interface 132 may be of a constant diameter and sized to fit within the aorta. The diameter of the aorta interface 132 can be between 0.5 and 2 inches. In some embodiments the diameter of the aorta interface 132 can be between 0.75 and 1.125 inches. Preferably, in some embodiments the diameter of the aorta interface is 0.75 inches, 0.875 inches, 1 inch, or 1.125 inches. The aorta interface 132 may be smooth or textured. FIG. 1 illustrates a texture 128 on the aorta interface 132 to help prevent the aorta from slipping off of the cannula body 114. In the embodiment shown in FIG. 1, the aortic cannula 100 is placed in the aorta so that the aorta does not rise above the end of the texture 128. FIG. 4 is a cross sectional view of one embodiment of the texture 128. The texture 128 may be of any shape. In one embodiment the texture 128 comprises concentric ridges extending around the aorta interface 132 that are sloped at a 45 degree angle on their lower side and are perpendicular to the cannula body 114 on their upper face. This design allows the aorta to slide onto the aorta interface 132 easily, but prevents the aorta from sliding off the aorta interface 132. Preferably the ridges are about 0.005 inches tall. However, one of skill in the art would understand that the texture features could be of any shape and size to allow the aorta to be situated around the aorta interface 132 and to help hold the aorta in place while minimizing damage to the tissue. In one embodiment, the radial edge of the aortic interface 132 does not have a ridge to minimize trauma to the tissue. Alternatively, one of skill in the art would recognize that a ridge could be designed to minimize tissue trauma and to hold the aorta in place.

Pivot Arm

A pivot arm 140 is coupled to the pivot mount 122. FIGS. 3*a-e* illustrate different views of a pivot arm and pivot arm strap (discussed below) in one embodiment. The pivot arm 140 allows the device 100 to adjust and grip aortas of different thicknesses. In one embodiment the cannula body 114 includes two pivot arms 140 coupled to two pivot mounts 122 on the cannula body. One of ordinary skill would understand that the number of pivot arms 140 corresponds to the number of pivot mounts 122. The pivot arm 140 comprises a grip pad 116, a sliding pivot window 118, and a strap 124. The sliding pivot window 118 allows the strap 124 to maintain uniform contact with the aorta through a range of motion. The grip pad 116 can be smooth, or contain features such as molded ridges or other texture to stop the user's fingers from slipping. The grip pad can be any shape, preferably round. In some embodiments the grip pad 116 may be detachable. In other embodiments a reusable tool that attaches to the pivot arms 140 could be used in place of the grip pads 116. The dowel pin 120 allows the pivot arm 140 to rotate around the dowel pin 120 when it is actuated. The pivot arm 140 is made from injection molded acetyl or any material with similar properties. One of skill in the art would recognize that while the sliding pivot provides certain advantages over a fixed pivot point, a fixed pivot point could also be used. Some embodiments may include a locking mechanism to hold the pivot arm 140 in an open position.

Pivot Arm Strap

The pivot arm strap 124 is coupled to the pivot arm 140. The pivot arm strap is best seen in FIGS. 1 and 3. As shown in FIG. 1, in one embodiment the cannula body 114 includes two pivot arm straps 124 coupled to two pivot arms 140. One of ordinary skill would understand that the number of pivot straps 124 corresponds to the number of pivot arms 140. The pivot arm strap 124 and the sliding pivot window 118 allow the cannula body 114 to uniformly grip the aorta. The pivot arm strap 124 is designed to be stiff enough to hold the aorta, while maintaining enough flexibility to conform to the aorta and minimize tissue damage. The pivot arm straps 124 are curved. The pivot arm strap 124 optionally has a loop 136 and a guide 142 to retain a cable tie (not shown) around the pivot arm strap 124. The cable tie is made from a flexible nylon material or material with similar properties. Once the cable tie has been threaded through the loop 136 and slotted in the guide 142, it is tightened to the desired tension. The amount that the cable tie is tightened is the same for all sizes of cannulas. Windows 126 in the pivot arm strap 124 normalize the pressure exerted on the aorta by altering the surface area of the strap in contact with the aorta. Accordingly, the size of the windows 126 vary depending on the size of the aorta. The size of the windows 126 are calculated so that when the cable tie is tightened, it exerts the same compression on the aorta for every size device 100. Thus, the compression exerted on the aorta holds it in place without damaging the tissue. One of ordinary skill would understand that alternatively, the cable tie may be tightened to a specific tension for each size of the device 100. In addition, other mechanisms of clamping to hold the aorta in place could be used in place of the cable tie, for example a hose clamp or a tension strap. Additionally, the pivot arm strap 124 and the windows 126 could be of different shapes and sizes. Alternatively, the windows could be omitted. One of skill in the art would also understand that the pivot arm 140 and the pivot arm strap 124 could be sections of a single piece. In addition, one of skill in the art would understand that the inner surface of the pivot arm strap 124 could be smooth, or textured for additional traction.

In one embodiment, the aorta is secured to the cannula body. The grip pad 116 is depressed by the user causing the pivot arm 140 to move around the sliding pivot window 118 and to compress torsional spring. The pivot arm 140 rotates around the dowel pin 120 in the sliding pivot window 118 and the pivot arm straps 124 move away from the cannula body 114, which makes room to place the cannula in the aorta in a preferred manner than if the pivot point were fixed. When the grip pad 116 is released the torsional spring (not shown) exerts pressure on the pivot arm strap 124 and temporarily holds the aorta in place. The straps closes on the aorta and the sliding pivot window 118 allows the pivot point to change in order to compensate for variations in tissue thickness and maintain alignment and concentricity of pivot arm 140 to cannula body 114 through the full range of rotation. This allows the strap 124 to seat uniformly on the aorta. Then, the cable tie is threaded through the loop 136 and between the guide 142. The cable tie is tightened to a predetermined tension. One of skill in the art would understand that the cable tie could be replaced with other mechanisms for securing the pivot arm straps 124. In some embodiments the cable tie can come preassembled in the loops 136.

Pledgets

In some embodiments, the user may suture surgical felt pledgets on the aorta. The pledgets serve as an additional measure to retain the aorta on the cannula body 114 because the pledgets provide a barrier that does not slide between the pivot arm strap 124 and the cannula body 114. Four sets of two (one inside, one outside) pledgets are equally spaced around the aorta and sutured. One of skill in the art will recognize that more or fewer pledgets may be used. In one embodiment, the aorta is positioned onto the cannula body 114 so that the pledgets are not directly above a space between the pivot arms 140 to prevent the pledgets from sliding through the space between the two sides of the pivot arm straps 124. It will be recognized by one of skill in the art that the pledgets may be placed anywhere on the aorta and end up in any orientation with respect to the pivot arm straps. The pledgets may be standard, surgical felt pledgets. Alternatively, they may be injected molded, rigid, elastomeric pledgets made of a high Durometer material, such as silicone, or a similar material. One of skill in the art would understand that the pledgets could be replaced with other materials that attach to the tissue, and that provide an anchor to prevent the device from sliding between the strap and the cannula body or damaging the tissue. Examples of these materials include, but are not limited to, a continuous ring of material that attaches to the tissue or a staple.

Tip Holder

Figure 6:
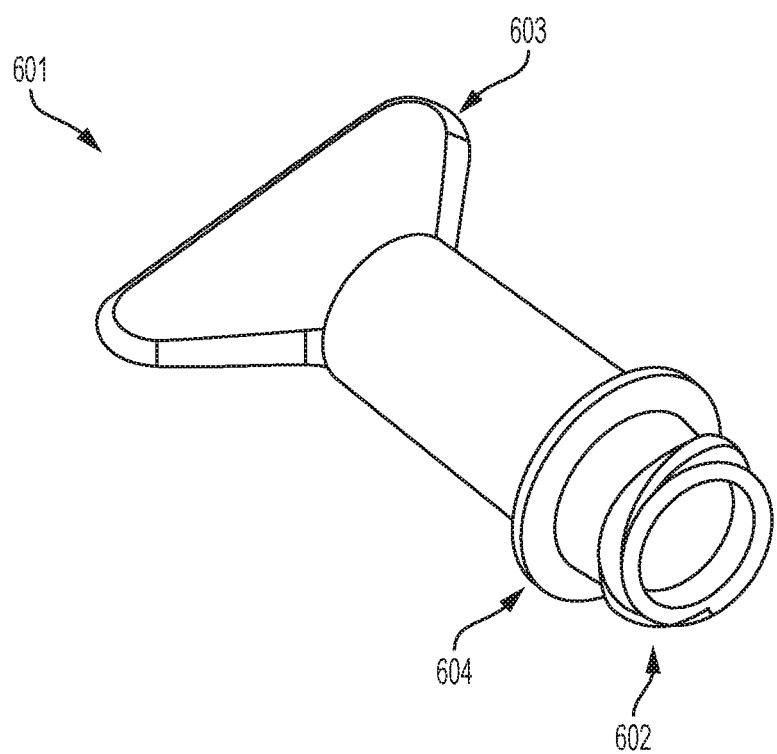
FIG. 6 illustrates a tip holder according to one embodiment.

FIG. 6 depicts a tip holder 601. The tip holder 601 is generally cylindrical, though it may have other shapes. The tip holder has a handle 603. The handle may take any shape that allows a user to hold the tip holder 601. The tip holder 601 can also have threads 602. The locking nut 102 can be screwed onto the threads 602. The tip holder 601 can also have a stopper 604 which protrudes from the tip holder 601 and serves as a stopping point for the locking nut 102. One of skill in the art would understand that other designs can be used to attach the locking nut to the tip holder. Alternatively, the tip holder may be secured to the aortic cannula 100 using other mechanisms known to one skilled in the art. Once secured, the tip holder can be used to hold the aortic cannula 100 with or without a heart positioned on the aortic cannula 100.

Example 1

The aortic cannula 100 may be used to connect a heart to an organ chamber (not shown). The aortic cannula 100 holds the aorta open and in place and allows perfusate to be perfused through the heart so the heart can be maintained in near physiologic conditions. In one embodiment, to deploy the aortic cannula, the user first selects an aortic cannula 100 that is sized to fit the heart. In one embodiment the aortic cannula 100 may be selected by measuring the aorta. The user depresses the thumb pads 116 on the spring-loaded pivot arms. When the user depresses the grip pads 116, the pivot arms 140 rotate around the dowel pin 120 within the sliding pivot window 118 and the pivot arm straps 124 move away from the cannula body 114 making room to place the cannula in the aorta. The user can place the cannula in the aorta. Then the user releases the thumb pads allowing the pivot arms 140 to close on the aorta. The pivot arms 140 may be operated at the same time or individually. The pressure created by the torsional springs temporarily holds the aorta in place. The user may adjust the aorta position, if necessary, such that aorta is fully engaged on the cannula body 114. Next the user places a cable tie through the loops 136 and guides 142 in the pivot arm straps 124. The user then tightens the cable tie to hold the aorta in place. In some embodiments the cable tie may be tightened using a tool which tightens the cable tie to a predetermined force. The user inserts the tapered fitting 108 into the organ chamber (not shown). Then the user tightens the locking nut 102. One of skill in the art will recognize that in some embodiments the aortic cannula 100 could first be seated in the organ chamber and then the aorta could be secured to the aortic cannula 100.

The invention claimed is:

1. An aortic cannula for use in an ex vivo organ care system comprising:
   a cannula body comprising:
      a fitting adapted to connect to an organ care system, and an aorta interface to contact an aorta;
   a pivot arm strap operably connected to a pivot mount, wherein the pivot mount allows the pivot arm strap to uniformly contact the aorta to hold the aorta on the aorta interface; and
   a spring which applies pressure to the pivot arm strap to hold the aorta on the aorta interface.

2. The aortic cannula of claim 1, further comprising a pivot arm connected to the pivot arm strap and to the pivot mount, such that when the pivot arm is moved toward the cannula body by rotation around the pivot mount the pivot arm strap moves away from the cannula body.

3. The aortic cannula of claim 2 wherein the pivot arm and the pivot arm strap are parts of a single piece.

4. The aortic cannula of claim 1 wherein a dowel pin communicates with the spring to allow the pivot arm to rotate around the dowel pin.

5. The aortic cannula of claim 2 wherein the pivot arm further comprises a grip pad used to depress the top of the pivot arm.

6. The aortic cannula of claim 5 wherein the grip pad is textured.

7. The aortic cannula of claim 5 wherein the grip pad is removable.

8. The aortic cannula of claim 1 wherein the pivot arm strap further comprises a loop and guide which retain a cable tie around the pivot arm strap.

9. The aortic cannula of claim 8 further comprising windows sized to normalize the compression exerted on the aorta by the cable tie such that the same amount of pressure will be exerted on the aorta regardless of the size of the pivot arm strap for a given cable tie tension.

10. The aortic cannula of claim 1 further comprising a connector used to reversibly secure the aortic cannula to an organ chamber.

11. The aortic cannula of claim 10 wherein the connector is a threaded locking nut.

12. The aortic cannula of claim 1 wherein the aorta interface is textured.

13. An aortic cannula for use in an ex vivo organ care system, comprising:
   a locking nut configured to reversibly secure the aortic cannula to an organ chamber assembly;
   a cannula body, comprising:
      a tapered fitting sized to connect to an organ chamber assembly;
      an aorta interface sized to fit within an aorta; and
      a tapered midsection extending from the tapered fitting to the aorta interface; and
      a pivot mount;
   a pivot arm operably connected to the pivot mount, the pivot arm comprising:
      a grip pad that can be used to depress a top of the pivot arm;
      a pivot arm strap configured to hold the aorta against the aorta interface; and
      a sliding pivot window configured to allow the pivot arm strap to maintain contact with the aorta through a range of motion; and
   a dowel pin allows the pivot mount to connect to the sliding pivot window;
   wherein the pivot arm is configured to rotate around the dowel pin.

14. The aortic cannula of claim 13 further comprising a tip holder configured to connect to the locking nut.

15. The aortic cannula of claim 13 wherein the aortic interface is textured.

16. The aortic cannula of claim 13 further comprising a spring which applies pressure to the pivot arm strap to hold the aorta on the aorta interface.

17. The aortic cannula of claim 16 wherein the grip pad compresses the spring when depressed.

18. The aortic cannula of claim 13 wherein the pivot arm strap further comprises a loop and guide which retain a cable tie around the pivot arm strap.

19. The aortic cannula of claim 18 further comprising windows sized to normalize the compression exerted on the aorta by the cable tie such that the same amount of pressure will be exerted on the aorta regardless of the size of the pivot arm strap for a given cable tie tension.

20. A method of using an aortic cannula to place a heart in fluid communication with an organ care system the method comprising:

selecting an aortic cannula sized to fit an aorta of the heart the aortic cannula comprising:

a cannula body comprising:

a fitting adapted to connect to an organ care system; and an aorta interface to contact an aorta; and a pivot arm strap operably connected to a pivot mount, wherein the pivot mount allows the pivot arm strap to uniformly contact the aorta to hold the aorta on the aorta interface;

depressing the pivot arm such that the pivot arm rotates around a dowel pin and the pivot arm strap moves away from the cannula body, wherein the dowel pin allows the pivot mount to operably connect to the pivot arm;

placing the aorta interface in the aorta;

releasing the pivot arm;

tightening a cable tie around the pivot arm strap to hold the aorta in place around the aorta interface; and inserting the tapered fitting into an organ care system.

21. The method of claim 20 further comprising the step of suturing surgical felt pledgets on the aorta before placing the aorta on the aortic cannula.

22. The method of claim 20 further comprising using a locking nut to reversibly secure the aortic cannula to the organ care system.

\* \* \* \* \*